United States Patent [19]

Karr et al.

[11] 4,280,512
[45] Jul. 28, 1981

[54] CARDIAC PACEMAKER ELECTRODE FOR TRANSVENOUS APPLICATION

[75] Inventors: Dieter E. Karr, Berlin, Fed. Rep. of Germany; Scott B. Shanks, Lake Oswego, Oreg.

[73] Assignee: Biotronik Mess-und Therapiegeräte G.m.b.H. & Co., Berlin, Fed. Rep. of Germany

[21] Appl. No.: 79,215

[22] Filed: Sep. 26, 1979

[30] Foreign Application Priority Data

Sep. 30, 1978 [DE] Fed. Rep. of Germany ....... 2843096

[51] Int. Cl.³ .............................................. A61N 1/04
[52] U.S. Cl. .................. 128/785; 128/419 P
[58] Field of Search ................... 128/419 P, 784, 785, 128/786

[56] References Cited

U.S. PATENT DOCUMENTS

| 3,754,555 | 8/1973 | Schmitt | 128/419 P |
| 3,814,104 | 6/1974 | Irnich et al. | 128/419 P |
| 4,011,875 | 3/1977 | Lehr et al. | 128/419 P |

FOREIGN PATENT DOCUMENTS

| 2149449 | 4/1972 | Fed. Rep. of Germany . | |
| 2375872 | 7/1978 | France . | |
| 284244 | 1/1971 | U.S.S.R. | 128/785 |

Primary Examiner—William E. Kamm
Attorney, Agent, or Firm—Spencer & Kaye

[57] ABSTRACT

In a cardiac pacemaker electrode for transvenous insertion including a lead, a wire spring arrangement in electrical contact with the lead for fastening the electrode in the heart, a hollow cylinder, a piston to which the wire spring arrangement is connected to project from one end of the piston and which is displaceably mounted in the cylinder and an extension position in which at least part of the wire spring arrangement is retracted fully into the cylinder and an extension position in which at least part of the wire spring arrangement projects out of the hollow cylinder for fastening into heart tissue, and a guide wire extending through the lead and movable relative to the lead against the piston for pushing it from its retraction position to its extension position, the interior wall of the cylinder is made of electrically conductive material and is permanently conductively connected, at one end of the cylinder, to the lead, and the electrode is composed of at least one resilient contact element which is electrically conductively connected with the wire spring arrangement and is constructed so that it permanently contacts a region of the interior wall of the hollow cylinder, the contact between the contact element and the interior wall region being essentially dot or line-shaped and being independent of external forces exerted on the spring arrangement.

8 Claims, 4 Drawing Figures

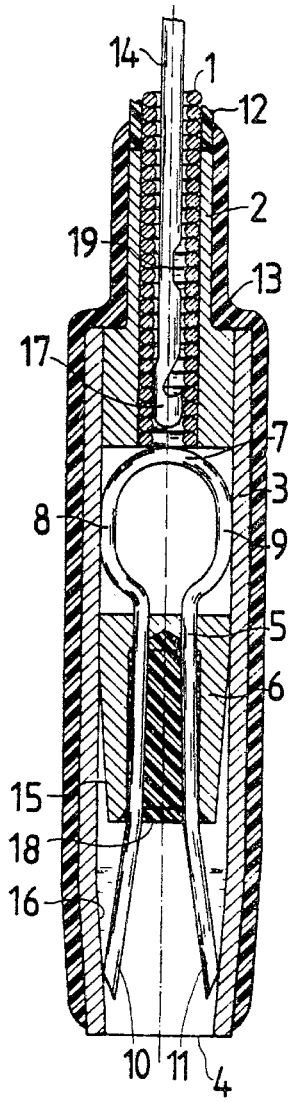
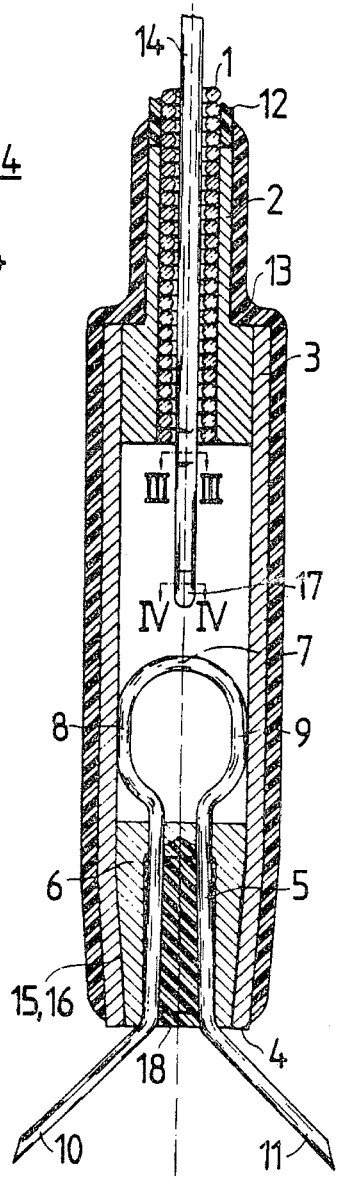
Fig. 1
Fig. 2
Fig. 3
Fig. 4

CARDIAC PACEMAKER ELECTRODE FOR TRANSVENOUS APPLICATION

BACKGROUND OF THE INVENTION

The present invention relates to a cardiac pacemaker electrode for transvenous application, the electrode being of the type including an insertion lead and a wire spring arrangement in electrical contact therewith for fastening in a heart wall. During the process of inserting such an electrode, the wire spring arrangement is held in a hollow cylinder and is connected with a piston which is displaceably mounted so that the pressure exerted on the piston by a guide wire conducted within the insertion lead causes the wire spring arrangement to exit from the hollow cylinder and to take on its position to engage in the cardiac tissue.

Such a cardiac pacemaker electrode is disclosed in U.S. Pat. No. 3,814,104. In that arrangement, there exists the drawback that, in the implanted state, reliable contact is not assured with certainty between the helical insertion lead and the wire spring arrangement which produces the actual stimulation in the cardiac tissue and is connected with the piston. Interruptions in the contact which interfere with the operation of the cardiac pacemaker, particularly in connection with the monitoring of the signals derived from the heart, and higher transfer resistances within the electrode arrangement reduce the voltage of the transmitted pulses so that their effect is reduced and proper cardiac stimulation is no longer assured.

In some types of pacemakers, such an increased transfer resistance can be compensated by an increase in the output pulse amplitudes. But the result of this is increased energy consumption and thus shorter life of the energy sources of the pacemaker, so that premature reimplantation may become necessary.

In the prior art electrode the ends of the wires forming the wire spring arrangement, when in the extended and thus spread open state, contact the electrically conductive hollow cylinder as soon as they are relaxed. But since the wire ends penetrate into the cardiac wall tissue to fix the electrode, they are guided essentially in an axial direction during penetration into the tissue. As a result, and considering the holding forces acting on them during the movement of the heart itself, they are only temporarily in secure mechanical, and thus electrical, contact with the front edge of the electrically conductive hollow cylinder. Since the conductive connection through the displaceable piston may also temporarily change its resistance value, there exists the danger of the creation of artifacts on the transmission path between the locus of stimulation and the pacemaker circuitry.

SUMMARY OF THE INVENTION

It is an object of the present invention to assure, within a cardiac pacemaker electrode of the above-mentioned type, secure contact during the entire period of pacemaker operation to provide reliable stimulation through the wire ends engaging into the tissue.

This and other objects are achieved, according to the invention, in a cardiac pacemaker electrode for transvenous insertion including a lead, a wire spring arrangement in electrical contact with the lead for fastening the electrode in the heart, a hollow cylinder, a piston to which the wire spring arrangement is connected to project from one end of the piston and which is displaceably mounted in the cylinder for movement between a retraction position in which the wire spring arrangement is retracted fully into the cylinder and an extension position in which at least part of the wire spring arrangement projects out of the hollow cylinder for fastening into heart tissue, and a guide wire extending through the lead and movable relative to the lead against the piston for pushing it from its retraction position to its extension position, by making the interior wall of the cylinder of electrically conductive material and permanently conductively connecting one end of the cylinder to the lead, and by constituting the electrode of at least one resilient contact element which electrically conductively connected with the wire spring arrangement and is constructed so that it permanently contacts a region of the interior wall of the hollow cylinder, the contact between the contact element and the interior wall region being essentially dot or line-shaped and being independent of external forces exerted on the spring arrangement.

The novel structure according to the invention effects a decoupling of the forces of the contact element from the wire spring arrangement which assures that the surface which produces the electrical contact between the cardiac tissue and the pacemaker and which is effective for stimulation remains essentially constant during operation of the pacemaker independently of stresses acting on the attachment of the electrode and that no part of this surface is intermittently "switched off" by only temporary establishment of contact. The contact element according to the invention, which preferably forms a type of "sliding contact", is pressed resiliently and constantly against the interior of the hollow cylinder, with an almost constant force.

A particular advantage of the invention is that this establishment of contact is also assured even when the fit of the piston in the cylinder varies within a certain tolerance range so that the entire structure including the wire spring arrangement, the piston and the resiliently contacting element is more easily displaceable than is an arrangement in which the constant electrical contact between the ends of the wires and the hollow cylinder must be assured by a correspondingly tightly fitted piston wall.

Such a reduction in friction during release of the wire spring arrangement which engages into the cardiac tissue is of significance because the helical insertion lead must be made of a particularly soft material so that the required freedom from breakage can be assured even in the face of the numerous bending stresses encountered during operation due to cardiac activity and arm movements of the person wearing the pacemaker. If a large pressure had to be exerted on the guide wire, or stylet, to extend the wire spring arrangement, the relatively soft helical lead would change its position and thus the electrode end would come to lie in a different region of the ventricle or of the auricle, respectively, and thus the threshold measurement effected with the wire ends still retracted would possibly no longer be valuable to determine the locus of fixation of the electrode.

According to an advantageous further embodiment of the present invention, the contact element and the wire spring arrangement form a unit which is brought through a corresponding opening extending in the longitudinal direction of the piston. This helps to simplify manufacture, resulting in a reduction in manufacturing costs. It is here also of advantage that the resilient lengths of the arrangement may be made contiguous and continuous in the longitudinal, or axial, direction so that better dimensional varieties become possible for the entire spring arrangement.

The region of the opening in the piston is closed, in order to seal it, with a suitable elastic filler, such as for example silicone rubber. The lengths of the wire ends or wire spring arrangement, respectively, extending through the silicone rubber then nevertheless are available as a resilient region.

If the contacting element or the region of the wire spring arrangement brought through the piston forms, in its rear area, a loop or eye which can be gripped and retracted by a guide wire equipped with a hook at its end, there exists the particular advantage that, in the event a first fastening of the electrode in the heart does not furnish satisfactory stimulation results, the wire spring arrangement can be retracted into the hollow cylinder for unimpeded movement and relocation of the electrode. If the electrode were withdrawn through the vein with the wire spring arrangement extended, there exists the danger of damage to vein and heart valves.

The gripping of the eye by means of the hook on the guide wire is facilitated if the end of the guide wire is given, in the area of the hook, a noncircular cross section, for example a flattened cross section or a cross section with an extension, so that the treating physician, once he has advanced the guide wire within the lead until it abuts the eye, rotates the stylet and feels the resistance offered against this rotation to thus determine the position of the hook with respect to the eye. The hook of the guide wire can then engage firmly in the eye and the guide wire need only be retracted to retract the wire ends until the rear end of the eye has reached the end of the lead and resists further retraction. This makes it easily possible for the physician fixing the electrode to blindly hook the guide wire into the eye in spite of the small dimensions of the arrangement.

Such an eye provided at a piston guided in a hollow cylinder is independent of the presence of a "slider" to improve contact and can be used with advantage independently of the configuration of a wire spring arrangement which penetrates the cardiac tissue.

It is of advantage if the piston sealingly contacts the interior of the hollow cylinder and thus forms a block against body fluids tending to enter into the interior of the hollow cylinder. For example, if the piston is made to be tapered in the direction toward the frontal face of the electrode and an area of the inner face of the cylinder which comes in contact with the piston area in the extended state of the wire spring arrangement is given a matching configuration, the piston and cylinder form a type of plug connection having a conical sealing surface and providing a particularly good sealing effect when the wire spring arrangement is extended in the operating state of the electrode. The protection of the interior of the electrode against penetrating body fluids secures the electrical contact between the inner wall of the hollow cylinder and the contact element permanently in contact therewith.

The prevention of the entrance of blood into the part of the helical lead near the heart is of particular importance since coagulation of the blood in this area would lead to stiffening of the electrode lead. Any stiffening would signify an increased force requirement for bending the lead with every heartbeat in that area of the lead which is most affected by such deformations. The increased force required for this bending is transferred as a pulling effect to the electrode fastening in the heart which is thus stressed to an undue degree so that dislocation may be the result.

It is particularly favorable that the type of seal employed does not contribute to an increase in friction when the wire spring arrangement is extended but in the end position assures a seal in an extremely reliable manner.

A simplification and shortening of the configuration of the electrode can be accomplished if the helical lead is given an appropriate diameter and the contact element directly contacts the interior of the helical lead as an extension of the hollow cylinder.

BRIEF DESCRIPTION OF THE DRAWINGS

FIG. 1 is a cross-sectional view of one preferred embodiment of a cardiac pacemaker electrode according to the present invention in the position for introduction through a vein.

FIG. 2 is a view similar to that of FIG. 1 of the same cardiac pacemaker electrode with the wire ends in the extended state.

FIGS. 3 and 4 are cross-sectional views, taken along lines II—III and IV—IV of FIG. 2, through a guide wire, a stylet used with the cardiac pacemaker electrode embodiment of FIGS. 1 and 2.

DESCRIPTION OF THE PREFERRED EMBODIMENTS

In the illustrated embodiment of the electrode according to the invention a lead 1 which leads to the cardiac pacemaker excitation pulse and monitoring circuitry (not shown) and establishes the electrical connection therewith is provided at its distal end with a sleeve 2 which is pushed onto the lead and is firmly connected with it by pressing, welding or the like. A hollow cylinder 3 is pushed over this sleeve 2 and is appropriately fastened thereto, the hollow cylinder 3 and the sleeve 2 being made of conductive material so that the frontal or distal end face 4 of cylinder 3 can suitably transmit electrical stimulation pulses to the cardiac tissue.

The hollow cylinder 3 encloses a cavity which is open in the direction toward the distal, or heart-side, end of the electrode arrangement and into which a wire spring arrangement 5 has been inserted. This arrangement itself is connected with a piston 6 which is arranged to be displaceable in the longitudinal, or axial, direction in the hollow cylinder 3.

The wire spring arrangement 5 is inserted through openings in the piston 6 and is provided, at its end facing away from the heart-side end of piston 6, with an eye or loop shaped part 7 which merges with contact the interior elements 8 and 9 of arrangement 5 which resiliently contact surface of the hollow cylinder 3.

At the distal end of the wire spring arrangement 5, two pointed wire ends 10 and 11 are provided which in the fixed state of the electrode engage into cardiac tissue. A mass 18 of silicone rubber fills a cavity formed in the interior of the piston 6. On the one hand, this filling mass permits elastic movement of the wire ends 10 and 11, while, on the other hand, it has a sealing effect so that body fluids cannot penetrate into the interior of the hollow cylinder 3 through the openings provided in the piston 6 for the wire spring arrangement 5.

Except for the area of the frontal face 4 which has a stimulating effect, the electrode arrangement is encased in an insulation which in the area of the helical lead 1 is provided in the form of an insulating sheath 12 and in the remaining area enclosing the sleeve 2 and the hollow cylinder 3 as a coating 13 of silicone rubber.

Suitable materials for the metal parts are the known physiologically compatible materials such as, for example, alloys known by the trade names Elgiloy and Protasul. For the selection of the material for the wire spring arrangement 5, the resiliency properties required to perform the functions to be described below must be considered.

A stylet 14 which serves to stiffen the electrode lead when the electrode is introduced through the vein simultaneously serves, in the illustrated embodiment, to extend and retract the wire ends 10 and 11 in a manner which will also be described in detail below.

During the introduction process, the wire spring arrangement 5 together with the wire ends 10 and 11 is in its retracted position in the hollow cylinder 3, shown in FIG. 1, so that the wire ends 10 and 11 cannot prematurely engage in the tissue. If, after the completion of a stimulation threshold measurement through the frontal face 4, a favorable position for fastening the electrode in the auricle or ventricle has been found, pressure is exerted on the stylet 14 from the opposite, or proximal, end of the electrode lead. This moves stylet 14 past the eye-shaped member 7 and in a known manner exerts a force on the rearward face of the piston 6 so that with the lead 1 held back the wire spring arrangement 5 together with the piston 6 can be displaced in the direction toward the cardiac tissue. When the wire ends 10 and 11 come to protrude through the opening in the hollow cylinder 3 beyond the frontal face 4, they have a tendency to spread open, due to their inherent spring bias, and to take on the position as shown in FIG. 2.

FIG. 2 shows the wire spring arrangement 5 in a completely extended state. The important thing is here that the piston 6 can be advanced to such an extent that its conical outer face 15 (FIG. 1) rests against the matching inner face of the tapered region 16 of the hollow cylinder. Due to the resulting sealing effect between piston 6 and hollow cylinder 3, no body fluid which could possibly adversely affect the electrical contact effect can enter into the area behind the piston 6 and from there into the region enclosed by the helical lead 1. The lateral areas of the wire spring arrangement 5 which form the resilient contacting elements 8 and 9 are always in firm contact with the inner wall of the hollow cylinder 3 so that a reliable contact is assured and any inward urging of the wire ends 10 and 11 even produces a lever action which augments the contact pressure.

The spring effect contributes to the fact that the piston 6 is not too easily displaceable, the fixing in the end position however being effected essentially by a "plug effect" of the contacting and tapered regions which form the seal as well as by the pulling force exerted on the wire ends 10 and 11 once they have been caught in the cardiac tissue.

The filling mass 18 of silicone rubber for the piston 6, on the one hand, seals the openings in the frontal face through which the wire spring arrangement 5 can pass against penetrating body fluids and, on the other hand, assures that arrangement 5 is firmly seated without limiting the flexibility of the wire ends.

If the first fixing of the electrode is not satisfactory, the electrode can be fastened at some other point in the heart without it being necessary to remove the electrode completely from the vein in order to bring the piston back into its starting position and thus retract the wire ends into the hollow cylinder 3. Such a withdrawal of the electrode with the wire ends telescoped out would additionally constitute a danger to the heart valves and the interior of the vein.

Due to the fact that, according to the invention, the stylet 14, which in FIG. 2 is rotated by 90° with respect to FIG. 1, has a hook-shaped portion 17, there exists the possibility of hooking the latter around the eye-shaped portion 7, and then retracting the stylet while holding lead 1 stationary to retract the wire spring arrangement 5 and the piston 6 back into the hollow cylinder 3 to re-establish the state shown in FIG. 1. This makes it possible to move the electrode back and forth in the vein without endangering any body tissue or parts. The engagement of the stylet 14 with the eye-shaped portion 7 in order to retract the wire spring arrangement 5 is facilitated if the hook-shaped region 17 of the stylet is formed to have a projecting portion in the form of a tongue 20. Alternatively, region 17 could be given a flattened portion similar to portion 19. In other words, region 17 is given a noncircular cross section as shown in FIGS. 3 and 4.

Thus rotation of the stylet within the lead is opposed by varying amounts of resistance when the hook-shaped portion is disposed in the region of the eye and contacts the side of it. In this way, the physician has an effective way to quickly and reliably sense, by feel, the angular position of the hook-shaped portion with respect to the eye so as to be able to perform the intended manipulations of the electrode without delay. If the tongue 20 which forms a projection contacts the eye, the direction of the hook can be recognized by increased resistance during rotation of the stylet 14. If the stylet 14 is precisely guided by the lead 1 in radial direction this changing resistance may result at least partly from the force necessary to move the loop-shaped member 7 out of its position. The nose may be replaced by bending the end of the stylet 14, where the hook is located, out of its straight direction in a way that a spring force is exerted by the stylet 14 against the eye-shaped portion, when it has been moved out of the lead 1 far enough and is bearing against the loop-shaped member 7.

Engagement of the hook-shaped portion 17 with the eye is facilitated by initially moving the stylet against the abutment formed by the rear face of the piston 6. In this case the flattened area 19 is located, as shown in FIGS. 1 and 2, to then contact the eye and clearly indicates the angular position of the hook by a certain detent effect during rotation of the stylet 14. With the stylet maintained in that position, it can be withdrawn to engage loop 7. The force relationships occurring after retraction from this position enable the physician to determine without difficulty whether the hook has engaged in the eye-shaped portion. For this function it is then sufficient to provide only the tongue 20 or the flattened portion 19.

Various design and embodiment possibilities also are conceivable within the scope of the invention for the resiliently contacting elements. For example, if the helical lead has an appropriate diameter, the eye-shaped portion may also slide within this lead so that the hollow cylinder can be shortened or possibly even eliminated completely.

It will be understood that the above description of the present invention is susceptible to various modifications, changes and adaptations, and the same are intended to be comprehended within the meaning and range of equivalents of the appended claims.

What is claimed is:

1. In a cardiac pacemaker electrode for transvenous insertion including a helical lead, a wire spring arrangement in electrical contact with the lead and including wire ends for fastening the electrode in the heart, a hollow cylinder, a piston to which the wire spring arrangement is connected so that the wire ends project from one end of the piston and which is displaceably mounted in the cylinder for movement, by means of a guide wire extending through the lead, between a retraction position in which the wire ends are retracted fully into the cylinder and an extension position in which the wire ends project out of the hollow cylinder and spread apart for fastening into heart tissue, and at least one contact element which is electrically conductively connected with the wire spring arrangement and is constructed so that it resiliently contacts a region which is in permanent electrical connection with the lead, the improvement wherein the outer lateral face of said piston tapers inwardly in the direction of the end thereof from which said wire ends project and the interior wall of said cylinder presents a correspondingly tapered surface located to sealingly contact said tapered lateral face of said piston when said piston is in its extension position for sealing the interior of said hollow cylinder against body fluids, the contact between said contact element and said region is independent of external forces exerted on said spring ends, and said contact element is disposed at a location at the interior of said hollow cylinder which is sealed against body fluids.

2. Cardiac pacemaker electrode as defined in claim 1 wherein said contact element has the form of a slider.

3. Cardiac pacemaker electrode as defined in claims 1 or 2 wherein the electrical connection between said contact element and said wire spring arrangement is made through said piston.

4. Cardiac pacemaker electrode as defined in claim 3 wherein said contact element is integral with said wire spring arrangement.

5. Cardiac pacemaker electrode as defined in claim 3 wherein said piston is provided with an opening through which extends the electrical connection between said wire spring arrangement and said contact element, and further comprising a mass of permanently elastic material sealing said opening in said piston.

6. Cardiac pacemaker electrode as defined in claim 5, wherein said contact element is integral with said wire spring arrangement.

7. Cardiac pacemaker electrode, as defined in claim 1 further comprising a loop-shaped member connected to said piston and spaced from the end of said piston, which is opposite the end from which said wire spring arrangement projects, and a guide wire provided with a hook-shaped member engageable with said loop-shaped member for enabling said guide wire to pull said piston from its extension position to its retraction position.

8. Cardiac pacemaker electrode as defined in claim 7 wherein said loop-shaped member constitutes a rear portion of one of said wire spring arrangement and said contact element.

* * * * *